United States Patent
Wu et al.

(10) Patent No.: US 10,174,306 B2
(45) Date of Patent: Jan. 8, 2019

(54) METHOD FOR PREPARING KAOLIN IMMOBILIZED GY2B BACTERIA AND APPLICATION THEREOF

(71) Applicant: SOUTH CHINA UNIVERSITY OF TECHNOLOGY, Guangzhou (CN)

(72) Inventors: Pingxiao Wu, Guangzhou (CN); Yuewu Li, Guangzhou (CN); Zhi Dang, Guangzhou (CN); Nengwu Zhu, Guangzhou (CN)

(73) Assignee: SOUTH CHINA UNIVERSITY OF TECHNOLOGY, Guangzhou, Guangdong Province (CN)

( * ) Notice: Subject to any disclaimer, the term of this patent is extended or adjusted under 35 U.S.C. 154(b) by 66 days.

(21) Appl. No.: 15/507,599

(22) PCT Filed: Dec. 3, 2014

(86) PCT No.: PCT/CN2014/092882
§ 371 (c)(1),
(2) Date: Feb. 28, 2017

(87) PCT Pub. No.: WO2016/029583
PCT Pub. Date: Mar. 3, 2016

(65) Prior Publication Data
US 2017/0283786 A1 Oct. 5, 2017

(30) Foreign Application Priority Data
Aug. 29, 2014 (CN) .......................... 2014 1 0438447

(51) Int. Cl.
C12N 11/14 (2006.01)
C12N 11/08 (2006.01)
C02F 3/34 (2006.01)
C12N 5/00 (2006.01)
C12N 11/02 (2006.01)
C12N 11/12 (2006.01)
C12N 1/20 (2006.01)
C12R 1/00 (2006.01)
C02F 101/34 (2006.01)

(52) U.S. Cl.
CPC ................ C12N 11/08 (2013.01); C02F 3/34 (2013.01); C12N 1/20 (2013.01); C12N 5/0018 (2013.01); C12N 11/02 (2013.01); C12N 11/12 (2013.01); C12N 11/14 (2013.01); C02F 2101/345 (2013.01); C12N 5/00 (2013.01); C12R 1/00 (2013.01)

(58) Field of Classification Search
CPC ...................................................... C12N 11/14
See application file for complete search history.

(56) References Cited

FOREIGN PATENT DOCUMENTS

CN 102674562 A 9/2012

OTHER PUBLICATIONS

Tao et al., "Rapid degradation of phenanthrene by unsing Sphingomonas sp. GY2B immobilized in calcium alginate beads," Int J Environ Res Public Heath 6:2470-2480, 2009.*
Cheng et al., "Biodegradation of crystal violet using Burkholderia vietnamiensis C09V immobilized on PVA-sodium alginate-kaolin gel beads," Ecotoxicology and Environmental Safety 83:108-114, 2012.*

* cited by examiner

Primary Examiner — Rosanne Kosson (57) ABSTRACT

Provided are a method for preparing kaolin immobilized GY2B bacteria and use thereof.

7 Claims, 7 Drawing Sheets

METHOD FOR PREPARING KAOLIN IMMOBILIZED GY2B BACTERIA AND APPLICATION THEREOF

TECHNICAL FIELD

The present invention relates to the technical field of microbial immobilization, particularly to a method for preparing kaolin immobilized GY2B bacteria and application thereof.

BACKGROUND ART

Phenol is an important organic raw material with a specific odor and a corrosivity, which is widely applied in the fields of medicine, resin, sterilizing agent, and the like. Phenol has a tremendous threat to human body, air and water body in the environment. When directly contacting with the human body, it will result in the corrosion on the in-vivo and in-vitro mucosa and skin, or even render the central nerve in a suppressed state, and in slow response to the external stimuli, and damage the liver and kidney functions, and the acute poisoning will even have fatal effect. It can not only contaminate rivers and lakes, destroy the ecological landscapes, inhibit the growth of aquatic animals and plants, or even lend to death, but also can migrate with the food chain, and damage the human health. The low concentration phenol pollution, which may result in the protein denaturation, and chronic poisoning due to the phenol accumulation caused by long-term drinking, may affect people's normal life activities, and the high concentration phenol pollution, which may result in the protein coagulation, render the body tissue injury and necrosis, and render acute poisoning, may become a threat to the life safety. In addition, due to the extremely high commonality and extremely high fluidity, phenol is listed as one of the 129 toxic pollutants and limited contaminants, therefore the treatments thereof have attracted a great attention.

The microbial degradation of the organic substances containing benzene ring, such as PAH, phenol, etc., has become an important means or even the preferred method for remediating the polluted environment in China and abroad. The biological treatment method has the advantages of low costs, slight interference on the environment, a variety of treatment forms, thorough treatments, etc. GY2B highly efficient degrading bacteria belong to *Sphingomonas paucimobilis*, which is screened and confirmed to have high or certain degradation capability on various polycyclic aromatic hydrocarbons, such as phenanthrene and the like. Degradation, which is achieved after bacterial intake and transformation, can effectively carry out ring-opening degradation, thus converting a variety of the organic contaminants containing benzene ring into simple, harmless, or easy-to-treat substances. Besides the aromatic hydrocarbon compounds, such as phenanthrene and the like, the GY2B bacteria have a significant degradation capability on phenol. At present, the degradation of the organic contaminants are mostly stayed at the addition of the bacteria alone and maintenance of the conditions, the ensurance and improvement of the degradation efficiency of the bacterial strain are also mostly related to the biological reinforcing agent, the suitable system conditions, the concentration of the bacteria, and the synergistic effect of the components.

SUMMARY OF THE INVENTION

Contents of the Invention

In order to solve the disadvantages and deficiencies in the art, such as long adaptive phase in the degradation process of the free GY2B bacteria, poor regulation ability in the complex and severe environment, and the like, the primary object of the present invention is to provide a method for preparing kaolin immobilized GY2B bacteria, which can significantly improve the degradation efficiency and rate of the GY2B bacteria, and maintain the degradation ability in certain severe environment.

Another object of the present invention is to provide the kaolin immobilized GY2B bacteria obtained by the above method.

Yet another object of the present invention is to provide use of the above kaolin immobilized GY2B bacteria.

In order to achieve the above objects, the technical solutions are applied in the present invention as follows.

A method for preparing the kaolin immobilized GY2B bacteria, comprises the steps of:

(1) the GY2B bacteria are activated and cultured, then are grown in an enrichment culture solution containing phenol, so as to obtain a concentrated bacterial solution; then the concentrated bacterial solution is centrifuged and washed with a sterile physiological saline, then the washed bacteria are suspended in a sterile physiological saline to obtain a bacterial suspension;

(2). a sterilized kaolin is dissolved in a sterile MSM culture solution, so as to form a suspension, then added in the bacterial suspension obtained in step (1) in a inoculation amount of 2~8%, adsorbed and immobilized for 1-4 hr, so as to obtain the kaolin immobilized GY2B bacteria.

Preferably, the activation and cultivation of the GY2B bacteria in step (1) are carried out as follows: 1-2 GY2B colonies stored in a plate are picked into a sterile MSM culture solution containing 50~200 mg/L phenol, shaken and cultured, at 25~35° C., 100~200 r/min, in dark, for 8~16 hr, then 1~2 mL of the bacterial solution is taken, and sub-cultured in a fresh sterile MSM culture solution containing 50~200 mg/L phenol for 8~16 hr, then 1~2 ml of the well grown bacterial solution is taken, and sub-cultured again in a fresh sterile MSM culture solution containing 50~200 mg/L phenol, repeat the sub-culture step as such 2-5 times (i.e., the steps of the sub-culture are repeated 2-5 times in the same conditions), so as to obtain a GY2B bacterial suspension having the ability to stably degrade phenol, which is plated and stored.

Preferably, in step (1), the bacteria are amplified in an enrichment culture solution containing 50~200 mg/L phenol for 8~16 h, so as to obtain the concentrated bacterial solution.

In step (1), the amplification culture of the bacteria in the enrichment culture solution containing phenol is to solve the deficiencies, such as fewer bacteria obtained from the cultivation in the inorganic salt culture solution, and while the preparation of the concentrated bacterial solution, maintain the degradation performance thereof.

Preferably, the concentration of the bacterial suspension obtained in step (1) is adjusted in an ultraviolet spectrophotometer at 600 nm to have an absorbance value of A=0.8~4.5. The obtained bacterial suspension is stored in a refrigerator at 2~10° C., for use.

Preferably, the centrifugation and washing in step (1) are carried out as follows: the centrifugation temperature is 2~10° C., the centrifugal speed is 6000~12000 r/min, the centrifuging time is 10~20 min, the number of the centrifuging and washing is 2-5 times.

Preferably, the sterilization of the kaolin in step (2) is carried out as follows: the kaolin is autoclaved at 100~150° C. for 15~60 min, then dried and dispersed at 80~150° C. for 10~30 min. The sterilized kaolin is cooled under the irradiation of ultraviolet light, for use.

Preferably, the kaolin in step (2) is of 100-300 meshes.

Preferably, the adsorption and immobilization in step (2) is carried out in a constant temperature shaking incubator, at 100~200 r/min, 25~35° C., in dark.

The kaolin immobilized GY2B bacteria are obtained according to the above method.

Use of the kaolin immobilized GY2B bacteria obtained according to the above method in treating the waste water containing phenol.

Preferably, when the kaolin immobilized GY2B bacteria are used in treating the waste water containing phenol, the system has a kaolin concentration of 15~30 g/L, a pH of 7~12, a phenol concentration of 0~300 mg/L. The system comprises the sterile MSM culture solution for dissolving kaolin, GY2B bacterial suspension and phenol-containing waste water.

As compared with the phenol degradation method by using the GY2B bacteria alone or other phenol degradation method, the present invention has the advantages and beneficial effects as follows.

(1). The adsorption and immobilization in the present method is easy to accomplish, convenient to operate, easy to obtain the raw materials, low prices, low costs, and mild degradation conditions, thus having great advantages in the practical application.

(2). As compared with the degradation by using the free bacteria, the present method can significantly improve the degradation efficiency and greatly increase the degradation rate, after immobilization, the degradation efficiency is increased by about 6~20%, and the degradation time can be shortened from about 10~48 hr to about 5~10 hr. The secondary product has little effects on the environment, due to the microbial degradation properties.

(3). The immobilized GY2B degrading bacteria of the present method can not only provide the promotion in the degradation efficiency, but also ensure the degradation performances of the bacteria in certain severe environment conditions, such as high concentration of phenol, alkaline environment, and the like, for example in a system having a pH of 9~12, and a phenol concentration of 200~300 mg/L, it can maintain the promotion effect in the degradation, and increase the degradation efficiency by 15~20%, and greatly reduce the degradation time, thus having great advantages in the practical application.

(4). The kaolin samples used in the present method are recovered and treated for reuse.

DETAILED DESCRIPTION OF THE INVENTION

Particular Embodiments

The present invention is further described in details below in combination of the examples and accompanying drawings, but the embodiments of the present invention are not limited thereto.

The MSM culture solution in the examples in the present invention comprises the components at concentrations as follows: 5.0 mL/L phosphate buffer solution (8.5 g/L $KH_2PO_4$, 21.75 g/L $K_2HPO_4.H_2O$, 33.4 g/L $Na_2HPO_4.12H_2O$, 5.0 g/L $NH_4Cl$), 3.0 ml/L $MgSO_4$ aqueous solution (22.5 g/L), 1.0 ml/L $CaCl_2$ aqueous solution (36.4 g/L), 1.0 ml/L $FeCl_3$ aqueous solution (0.25 g/L), 1.0 ml/L trace element solution (39.9 mg/L $MnSO_4.H_2O$, 42.8 mg/L $ZnSO_4.H_2O$, 34.7 mg/L $(NH_4)6Mo_7O_{24}.4H_2O$), the pH is adjusted to 7.2; the above MSM culture solution is autoclaved so as to obtain a sterile MSM culture solution required for the tests, wherein the expression "ml/L" refers to the added amount of the formulated component solution in 1 L of the final mixing solution, for example, 5.0 ml/L phosphate buffer solution refers to the added amount of 5 mL the buffer solution in 1 L of the finial mixing solution.

The sterile MSM culture solution containing 100 mg/L phenol in the examples of the present invention is prepared by the steps of: an amount of phenol is weighed into a beaker, dissolved in the above MSM culture solution, and transferred into a volumetric flask, brought to the isovolumetric volume with the above MSM culture solution to have a phenol concentration of 1 g/L, pipetted out 10 mL the isovolumetric solution, filter-sterilized, then added into an autoclaved MSM culture solution to have the final phenol concentration of 100 mg/L, so as to obtain the sterile MSM culture solution containing 100 mg/L phenol.

The enrichment culture solution in the examples of the present invention comprises the components as follows: 10 g peptone, 5 g beef extract, 5 g NaCl, 1 L distilled water, and the pH is adjusted to 7.0; the above enrichment culture solution is sterilized, then added the filter-sterilized phenol solution to have a final concentration of 100 mg/L, so as to obtain the enrichment culture solution containing 100 mg/L phenol required for the tests.

The GY2B bacteria in the examples of the present invention are separated and purified from the contaminated soil commonly found in the area in South China. The test samples are collected from the farmland soil near Guangzhou Petrochemical Plant (S), the soil near Guangzhou Oil-Gas plant (Y), and the soil near a wood preservative treatment plant (M), respectively (i.e., three bacterial samples are collected for each case, and carried out the steps of separation, purification, enrichment, etc., so as to finally obtain the selected bacteria which have the optimal degradation efficiency). The bacteria are purified by Dang Zhi Research project Group in School of Environment and Energy in South China University of Technology, and stored.

Example 1

A method for immobilization of GY2B bacteria with kaolin, comprises the steps of:

(1). activation and cultivation of GY2B bacteria: one to two GY2B colonies stored in a plate were picked into a sterile MSM culture solution containing 100 mg/L phenol, shaken and cultured in a shaker at 30° C., 150 r/min, in dark, for 12 hr, then taken a small amount of the bacteria solution (inoculation amount of 4%), and sub-cultured in a fresh sterile MSM culture solution containing 100 mg/L phenol, and repeated the sub-culture as such 3 times, so as to obtain the GY2B bacteria having the ability to stably degrade phenol, which was plated and stored;

(2). preparation of bacteria suspension: one to two plaques of the colonies activated and cultured in step (1) were picked into the enrichment culture solution containing 100 mg/L phenol, cultured for 12 hr at the same conditions, so as to obtain a concentrated bacterial solution; the concentrated bacterial solution was washed with a physiological saline and centrifuged three times, at 4° C., 8000 r/min, for 15 min; the washed bacteria were suspended in a physiological saline, so as to obtain a bacterial suspension, the concentration of the bacterial suspension was adjusted in an ultraviolet spectrophotometer at 600 nm, to have an absorbance value of A=1; the bacterial suspension was stored in a refrigerator at 4° C., for use;

(3). sterilization of kaolin: the natural kaolin commonly found in the area in South China were pulverized, ground, and sieved through 200-mesh sieve; 2 g kaolin was weighed into a 250 mL conical flask, autoclaved at 120° C. for 30 min, then dried and dispersed in an oven at 120° C., for 15 min, then cooled to room temperature on a sterile operating table under ultraviolet irradiation, for use;

(4). adsorption and immobilization of GY2B bacteria: 86 mL the sterile MSM culture solution (prepared by autoclaving the MSM culture solution in step (1)) was added into the sterilized kaolin in step (3), fully shaken and dispersed so as to obtain a kaolin suspension, then added 4 mL the bacterial suspension prepared in step (2); shaken in a constant-temperature shaking incubator in dark for 2 hr to arrive at the adsorption equilibrium between the kaolin and the GY2B bacteria, so as to obtain the required composite system (i.e., the kaolin immobilized GY2B bacteria), wherein the operation conditions for the constant-temperature shaking incubator were in consistent with those in the activation and cultivation of GY2B bacteria in step (1).

a. Detection of the Phenol Degradation Rate of the Activated and Cultured GY2B Degrading Bacteria in Step (1).

The autoclaved MSM culture solution, the bacterial solution, the filter-sterilized phenol mother solution were added sequentially in a 250 mL vessel, to bring the final system volume up to 100 mL, wherein the added amount of the bacterial solution was 4%, i.e., 4 mL, the phenol concentration was 100 mg/L, then shaken and cultured in a constant temperature shaking incubator, at 30° C., 150 r/min. The samples were taken regularly every two hours for detecting the residual phenol concentration in the system. The samples were treated by centrifuging at 10000 r/min, then the supernatants were diluted in a suitable ratio, and determined in an ultraviolet spectrophotometer at a wavelength of 270 nm. The phenol concentrations were calculated from the standard curve. The degrading equilibrium was achieved when the system concentrations were detected to have no change any more.

Finally, it was determined that the activated and cultured GY2B degrading bacteria in step (1) can complete the degradation of phenol in 12 hr, with a degradation rate of 86%-88%. The degradation rate of phenol $\Phi$ was calculated from the following equation:

$\Phi$=(the initial phenol concentration in the system $C_0$–the final phenol concentration in the system $C_1$)/the initial concentration $C_0$*100% b. Detection of the Phenol Degradation Rate of the Kaolin Immobilized GY2B Bacteria Prepared in Step (4)

2 g kaolin was accurately weighed, autoclaved, and dried in an oven at 120 degree, cooled to room temperature under an ultraviolet light. Then the sterilized MSM culture solution, and the bacterial solution were sequentially added, shaken in a constant-temperature shaking incubator at 30° C., 150 r/min for 2 hr to arrive at the adsorption equilibrium between the bacteria and the kaolin. Then the filter-sterilized phenol mother solution was added, and brought the final system volume up to 100 ml, wherein the added amount of the bacterial solution was 4%, i.e., 4 ml, and the phenol concentration was 100 mg/L. The system was shaken and cultured in a constant-temperature shaking incubator, and the following steps were in consistent with those in the detection of the phenol degradation rate of the free GY2B bacteria.

Finally, it was determined that the kaolin immobilized GY2B bacteria prepared in step (4) can complete the degradation in only about 6 hr, which was much faster than that of the free bacteria (12 hr). The time for completing the phenol degradation in the system was recorded as follows: the samples were taken regularly, and determined the residual phenol level in the system, the phenol concentrations were significantly reduced in the early stage, and when the phenol concentrations in the system were maintained at a low level and were not reduced any more in the later time, it was shown that the degradation was completed, and this time was defined as the phenol degradation time.

So the GY2B degrading bacteria had a good degradation effect. However, the kaolin immobilized GY2B bacteria prepared in step (4) had a stronger adaptive ability against the system environment, and provided a more stable degradation environment in the degradation process. The addition of kaonlin in the present invention can greatly reduce the adaptive phase of the GY2B degrading bacteria, therefore the composite system can complete the phenol degradation more faster in the practical application.

Example 2

The activation and cultivation of GY2B bacteria, preparation of bacterial suspension, and sterilization of kaolin in this example were the same as those in example 1, the differences lied in that various amounts of kaolin by mass were added in the adsorption and immobilization of the GY2B bacteria in this example to illustrate the effects of the kaolin on the degradation efficiency and rate of the GY2B bacteria. This example was carried out as follows:

The activation and cultivation of GY2B bacteria and preparation of the bacterial suspension were carried out according to the steps (1) and (2) in example 1, then 0 g, 0.01 g, 0.2 g, 0.5 g, 1 g, 2 g, 3 g of 200-mesh kaolin were accurately weighed into a 250 mL conical flask respectively, before sterilization, each group of kaolin was treated according to step (3) in example 1, then 86 mL the sterile MSM culture solution was added into each flask, fully shaken and dispersed, so as to form a kaolin suspension; then 4 mL the bacterial suspension was added into each group of the suspension, finally 7 groups of the samples were shaken in a constant temperature shaking incubator for 2 hour (30° C., 150 r/min, in dark), to arrived at the adsorption and immobilization equilibrium therebetween, so as to obtain 7 groups of the kaolin immobilized GY2B bacteria required for the tests.

7 conical flasks filled with the prepared kaolin immobilized GY2B bacteria were removed to a sterile operating table, 10 mL 1 g/L the filter-sterilized phenol solution was added into each flask, brought the final system volume up to 100 mL, shaken to uniform, wherein the phenol concentration in the final system was 100 mg/L, and the inoculation amount of GY2B bacteria was 4%. Each sample was carried out in triplicate, cultured in a constant-temperature shaking incubator in dark, wherein the instrument parameters were in consistent with those disclosed above.

Figure 1:
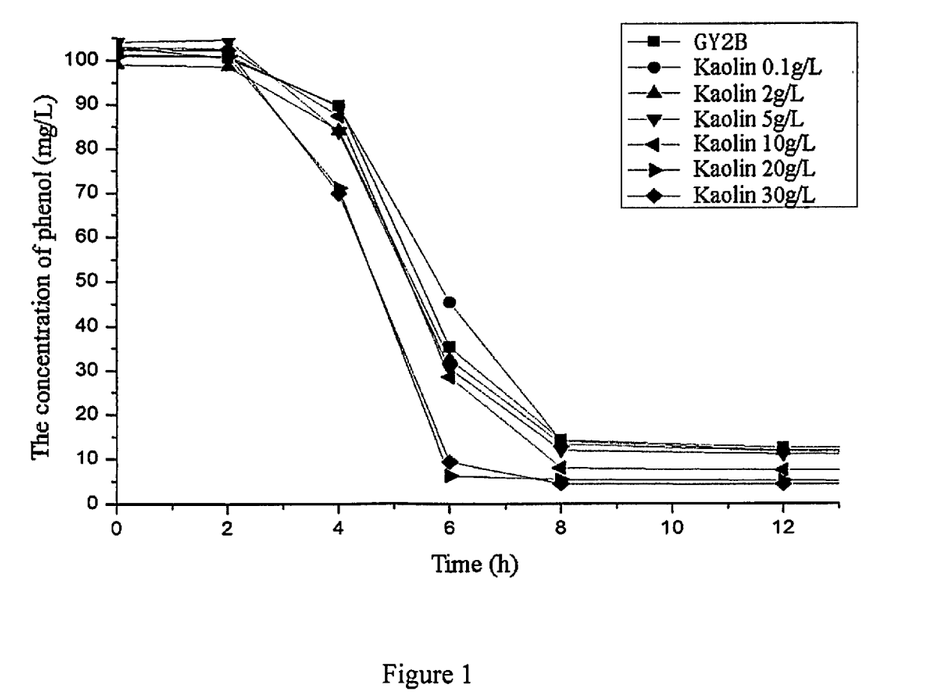
FIG. 1 shows the effects of various addition amounts of kaolin on the degradation efficiency and rate of the GY2B bacteria in example 2.

The samples were taken every 2 hr for determination of the residual phenol level in the system, wherein the samples were treated at 4° C., centrifuged at 10000 r/min for 5 min, taken the supernatant, diluted and determined in an ultraviolet spectrophotometer, at a wavelength of 270 nm. The phenol concentrations in the system were calculated from the standard curve, plotted according to the test results to illustrate the effects of the real-time phenol concentration and kaolin in each system on the degradation ability of the bacteria, as shown in FIG. 1. From FIG. 1, it can be found that too low added amount of kaolin in the adsorption and immobilization of GY2B bacteria, such as 0.1 g/L, had no significant promotion effects on the degradation ability of the GY2B bacteria, even showed inhibition to some extent. With the increase in the added amount of kaolin, the degradation effects were increasing, which showed the positive correlation between the increase in the degradation ability due to the immobilization of the GY2B degrading bacteria and the added amount of kaolin, wherein the added amount was 20 g/L, the promotion effect reached the optimal level, hereinafter further increase of the added amount of kaolin had no significant increase in degradation efficiency and rate any more. The added amount of kaolin was determined to 20 g/L by combining the effects and the used amount of the material Furthermore, the effects of the kaolin alone on the phenol adsorption were further illustrated as follows.

0 g, 0.01 g, 0.1 g, 1 g, 2 g of 200-mesh kaolin were accurately weighed into a 250 mL conical flask respectively, sterilized according to the step (3) in example 1; then added 90 L the sterile MSM culture solution into each flask, fully shaken and dispersed, so as to form a kaolin suspension, then added 10 mL 1 g/L the filter-sterilized phenol solution respectively, brought the final system volume up to 100 mL, wherein the phenol concentration was 100 mg/L. 5 groups of the samples were shaken in a constant temperature shaking incubator, at 30° C., 150 r/min, in dark. The samples were taken every 2 hr for determination of the residual phenol level in the mixing system, wherein the samples were treated at 4° C., centrifuged at 10000 r/min for 5 min, taken the supernatant, diluted, and determined, so as to explore the effects of kaolin alone on the phenol adsorption. The ultraviolet spectrophotometer had a determination wavelength of 270 nm. The phenol contents were calculated from the standard curve, plotted to show the adsorption dynamics, as shown in FIG. 2.

Figure 2:
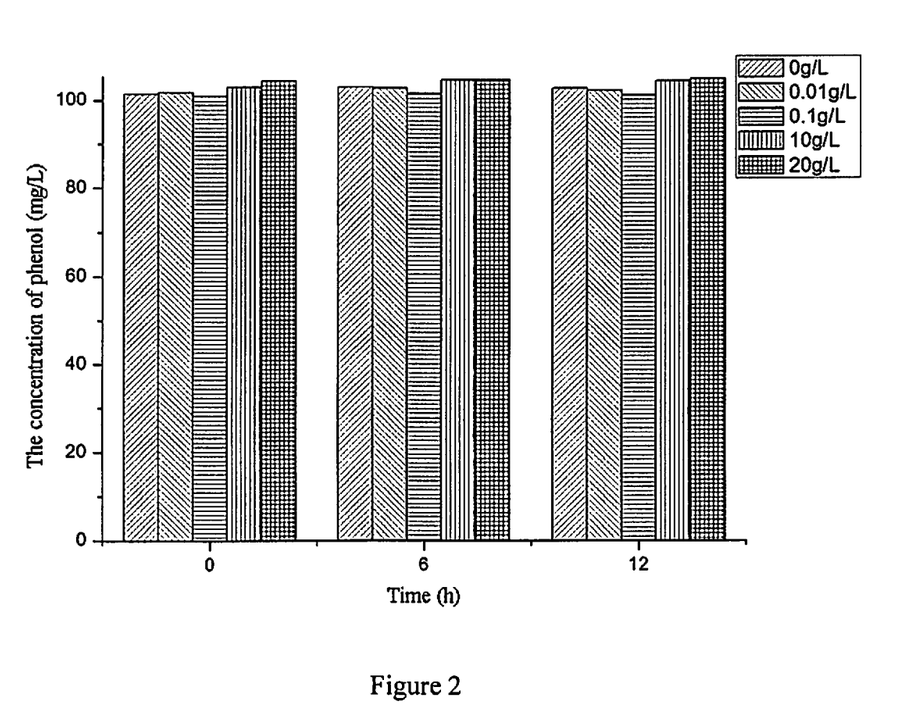
FIG. 2 shows the effects of various concentrations of kaolin on the adsorption of phenol in example 2.

From FIG. 2, it was found that either the high addition amount kaolin system or the low addition amount kaolin system, during the period from the beginning to the time that the degradation was completed in the normal condition, the phenol concentrations in the system had no significant change, which illustrated that the kaolin alone substantially had no effects on the phenol adsorption, which also excluded that the increases in effects of the kaolin immobilized GY2B bacteria composite system on the treatment of phenol were due to the phenol adsorption effect of the kaolin. Therefore, addition of kaolin for adsorption and immobilization of GY2B bacteria can increase the degradation rate and degradation efficiency of the degrading bacteria.

Example 3

The activation and cultivation of GY2B bacteria, preparation of bacterial suspension, and sterilization of kaolin in this example were the same as those in example 1, the differences lied in that various concentrations of phenol were treated in this example to illustrate the effects of the adsorption and immobilization of kaolin on the degradation ability of GY2B bacteria, in various initial phenol concentration, especially in high concentration. This example was carried out as follows.

The activation and cultivation of GY2B bacteria, and preparation of the bacterial suspension were carried out according to steps (1) and (2) in example 1, 4 parts of each 2 g kaolin were accurately weighed, and filled in four 250 ml conical flasks respectively, and before sterilization, each group of kaolin was treated according to step (3) in example 1; then added 86 mL, 81 ml, 76 mL, 71 ml the sterile MSM culture solution respectively, fully shaken and dispersed so as to form a kaolin suspension, then each added 4 mL the bacterial solution, mixed to uniform, then shaken in a constant-temperature shaking incubator for 2 hr at 0° C., 150 r/min, in dark, to reach the adsorption and immobilization equilibrium between the GY2B bacteria and the kaolin, so as to prepare four groups of the kaolin immobilized GY2B bacteria required for the tests.

After the immobilization and adsorption had be completed to prepare the kaolin immobilized GY2B bacteria required for the tests, four conical flasks were removed to a sterile operating table, each added 10 ml, 15 ml, 20 ml, 25 ml of 1 g/L the filter-sterilized phenol solution, brought the final total system volume up to 100 mL, shaken to uniform, wherein the phenol concentrations in the final system were 100 mg/L, 150 mg/L, 200 mg/L, 250 mg/L respectively, and the inoculation amount of the GY2B bacteria was 4%. Each sample was carried out in triplicate, and the free GY2B bacteria (i.e., the activated and cultured GY2B bacteria) control was set for each concentration, cultured in a constant temperature shaking incubator at 30° C., 150 r/min, in dark. Samples were taken every 2 hr for determination of the residual phenol level in the system, wherein the samples were treated at 4° C., centrifuged at 10000 r/min for 5 min, taken the supernatant, diluted, and determined in an ultraviolet spectrophotometer, at a wavelength of 270 nm. The phenol concentrations in the system were calculated from the standard curve. The changes of the phenol concentration in the system reflected the degradation capability of the immobilized GY2B bacteria in a high concentration of phenol, as shown in FIG. 4, and the degradation capability of the free GY2B bacteria in a high concentration of phenol as shown in FIG. 3.

Figure 3:
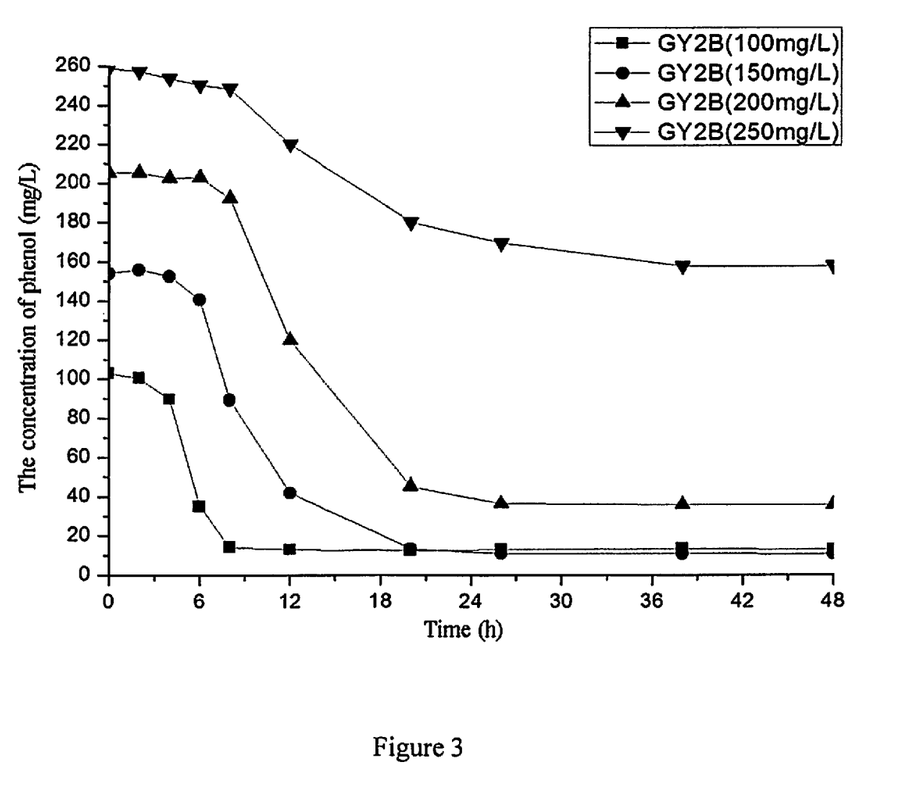
FIG. 3 shows the effects of the free GY2B bacteria on the degradation of high concentration phenol system in example 3.
Figure 4:
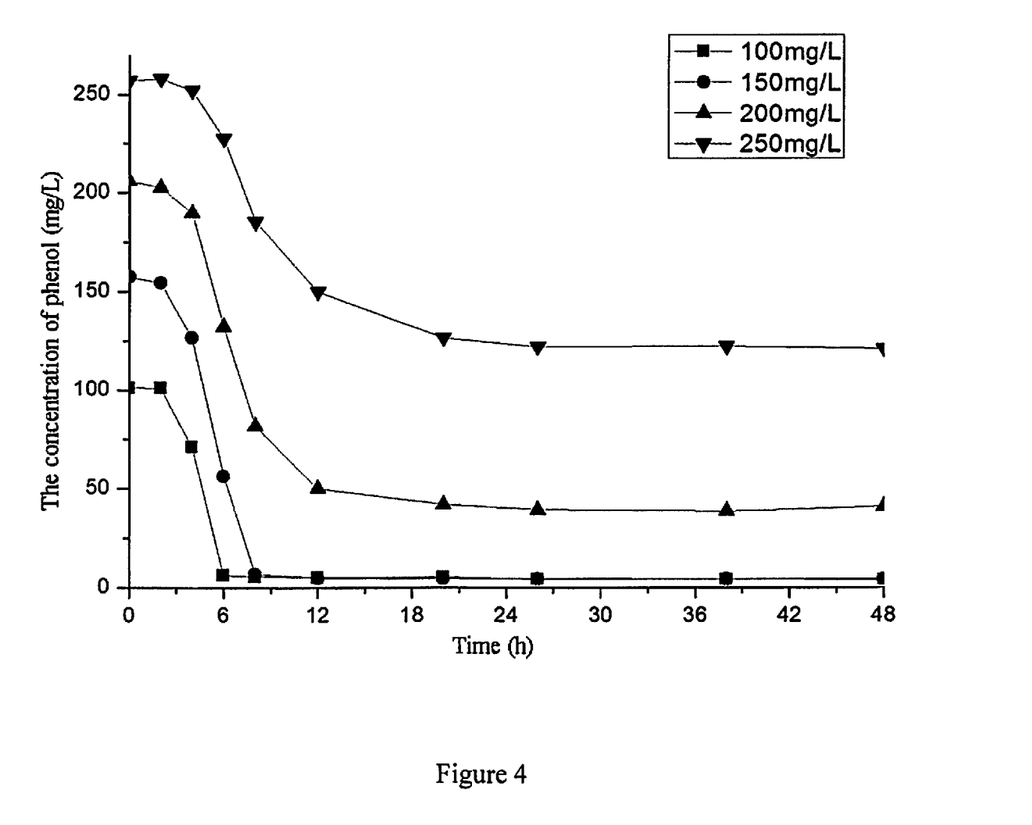
FIG. 4 shows the effects the kaolin/GY2B composite on the degradation of the high concentration phenol system in example 3.

As shown in FIG. 3, the free GY2B bacteria had longer adaptive period in high concentration of phenol, when the phenol concentration was higher than 150 mg/L, the degradation time for the free GY2B bacteria was more than 20 hr, or even when the phenol concentration was 250 mg/L, the degradation time was more than 36 hr; and the final degradation rate was low; when the phenol concentration was higher than 250 mg/L, the degradation rate was less than 50%. As shown in FIG. 4, the kaolin adsorbed and immobilized GY2B bacteria greatly reduced the degradation time, in the extremely high concentration of phenol, the system could complete the degradation in about 20 hr, and had a significant increase in the degradation rate, as compared with that of the free GY2B bacteria Example 4

The activation and cultivation of GY2B bacteria, preparation of bacterial suspension, and sterilization of kaolin in this example were the same as those in example 1. The differences lied in that various pH values were used in this example to illustrate the enhancing effects of the adsorption and immobilization of kaolin on the degradation capability of GY2B bacteria, and especially this example focused on the differences between the immobilized system and the free bacterial system under alkaline conditions.

The activation and cultivation of GY2B bacteria and preparation of bacterial suspension were carried out according to the steps (1) and (2) in example 1, then carried out the steps of:

(1) a sufficient amount of MSM culture solution were metered into seven conical flasks respectively, adjusted the pH with NaOH and HCl to 1, 3, 5, 7, 8, 10, 12 respectively, at the same time, prepared seven conical flasks into each of which 2 g kaolin was accurately weighed, and the above flasks were autoclaved together at 120° C. for 30 min, then removed the flasks filled with the sterilized MSM culture solutions having different pH to a sterile operating table, cooled to room temperature under ultraviolet light, the conical flasks filled with kaolin were dried and dispersed in an oven 120° C., then cooled to room temperature under ultraviolet light;

(b) the seven sterilized MSM culture solutions having different pH in step (a) were pipetted out 86 mL from each, added to the sterilized kaolin respectively, fully shaken and dispersed so as to form a kaolin suspension, then each added 4 mL the bacterial suspension, mixed to uniform, and shaken in a constant-temperature shaking incubator for 2 hr (30° C., 150 r/min, in dark) to reach the adsorption and immobilization equilibrium therebetween, so as to prepare 7 groups of kaolin immobilized GY2B bacteria having different pH;

(c) 7 groups of phenol mother solutions were taken each in a slight excessive amount, and adjusted the pH to 1, 3, 5, 7, 8, 10, 12, respectively, with NaOH and HCl solution, under a pH meter, filter-sterilized in a sterile operating table, then added 10 mL of the same into the conical flask filled with the kaolin immobilized GY2B bacteria having the corresponding pHs, respectively, brought the final system volume up to 100 mL, mixed to uniform, wherein the final bacterial inoculation amount in the 7 groups of sample systems was each 4%, and the phenol concentration was each 100 mg/L, cultured in a constant-temperature shaking incubator at 30° C., 150 r/min, in dark. The samples were taken every 2 hr for determination of the residual phenol level in the system, wherein the samples were treated at 4° C., centrifuged at 10000 r/min for 5 min, taken the supernatants, diluted, and determined in an ultraviolet spectrophotometer at a wavelength of 270 nm. The phenol concentrations in the system were calculated from the standard curve, and plotted, the results were shown in FIG. 6, the free GY2B bacteria (i.e., the activated and cultured GY2B bacteria) control test in the same test condition was set for each sample, and the test results were shown in FIG. 5.

Figure 5:
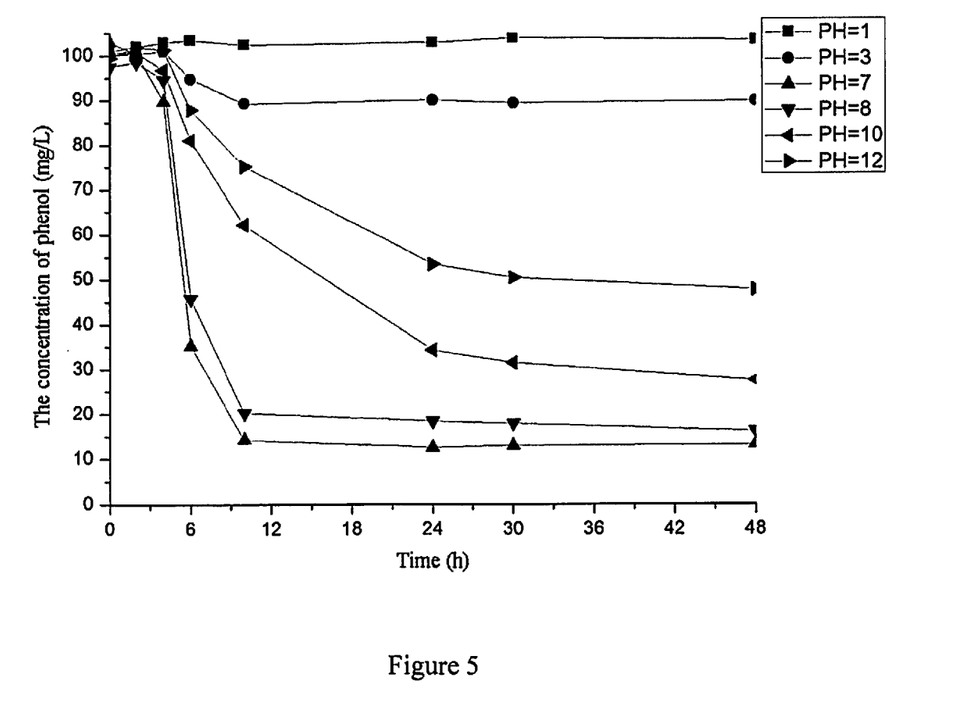
FIG. 5 shows the effects of the free GY2B bacteria on the degradation of phenol at various pHs in example 4.
Figure 6:
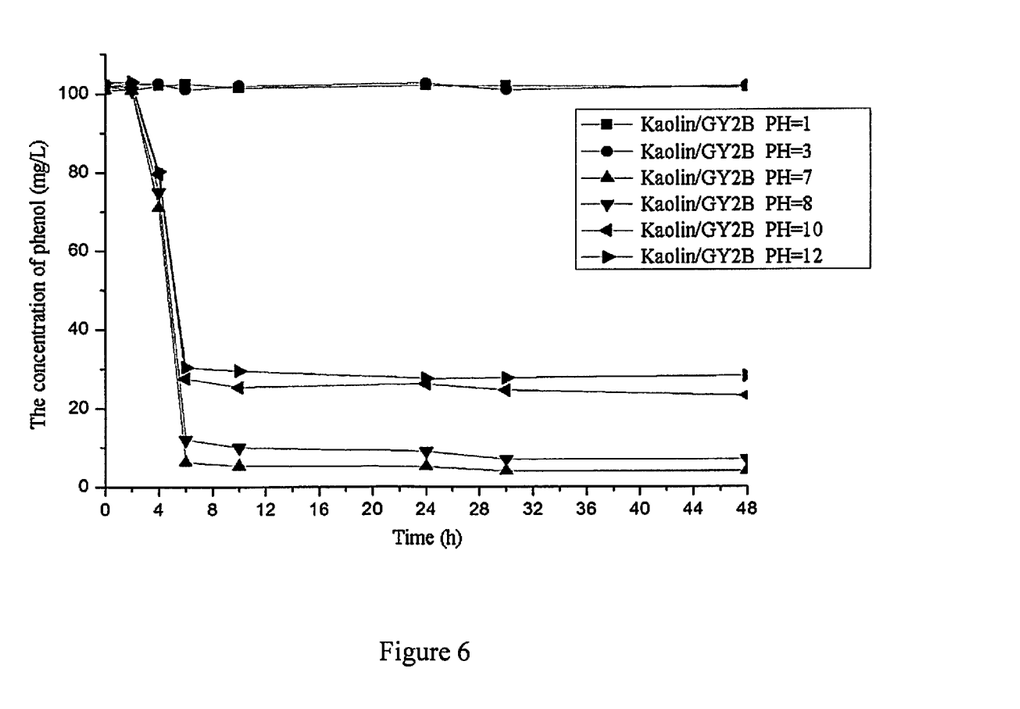
FIG. 6 shows the effects of the kaolin/GY2B composite on the degradation of phenol at various pHs in example 4.

As shown in FIGS. 5 and 6, at pH=7 and 8, both the kaolin immobilized GY2B bacteria and the free GY2B bacteria had high degradation efficiency, and the immobilization of kaolin had significant improvements in the degradation efficiency and rate. In the acidic pH conditions, both the activity and degradation ability of the bacteria were greatly suppressed, when the acidity was very higher, the system substantially lost the degradation effects on phenol, and the protection effects of the adsorption and immobilization of kaolin on the degradation ability were also lost. However, in the basic system conditions, the bacteria still maintained a certain degradation ability, the corresponding adaptive period was increased due to the severe conditions. The kaolin immobilized GY2B bacteria still had significant increase and protection in the degrading capability in the basic conditions, when pH was 12, the free GY2B bacteria had a long degradation period for reducing the phenol concentration in the composite system to about 50%, and the kaolin immobilized GY2B bacteria degraded about 70% phenol in the system in 6 hr, thus showing a significant increase effect.

Example 5

The activation and cultivation of GY2B bacteria, preparation of bacterial suspension, and sterilization of kaolin in this example were the same as those in example 1, the differences lied in that the degradation effects of the kaolin which were reused several times were tested in this example to illustrate the reuse effects of the used kaolin.

The activation and cultivation of the GY2B bacteria and the preparation of the bacterial suspension were carried out according to steps (1) and (2) in example 1, then carried out the step of:

(a) 2 g kaolin were accurately weighed into a 250 mL conical flask, autoclaved at 120□ for 30 min, dried and dispersed in an oven at 120° C., and cooled to room temperature under ultraviolet light;

(b) 86 mL the sterile MSM culture solution was added into the sterilized kaolin in step (a), fully mixed to uniform, so as to form a kaolin suspension, then added 4 mL the bacterial suspension, shaken in a constant temperature shaker for 2 hr (30° C., 150 r/min, in dark) to reach the absorption and immobilization equilibrium, then added 10 mL 1 g/L the filter-sterilized phenol solution, brought the final system volume up to 100 mL, wherein the final bacterial inoculation amount was 4%, the final phenol concentration in the system was 100 mg/L, then cultured in a constant temperature shaking incubator. Samples were taken every two hours for determination of the phenol content, wherein the sample were treated by centrifuging at 10000 r/min, at 4° C. for 5 min. The determination was carried out in an UV spectrophotometer at 270 nm wavelength;

(c) after the degradation of the system in step (c) was completed, taken out and stood for 6 hr, removed the supernatant, washed and centrifuged the underlying deposited clays with distilled water 3 times, at 4000 r/min, 4° C., for 10 min, then collected the washed kaolin, and dried in a oven at 105° C., ground into fine powders in a mortar, for use.

(d) 2 g the recovered and treated kaolin in step (c) were weighed into a 250 mL conical flask, repeated the systemic treating processes of (a) sterilization of kaolin and (b) degradation of phenol. The changes in the phenol concentration were determined in the kaolin application system in each time.

Figure 7:
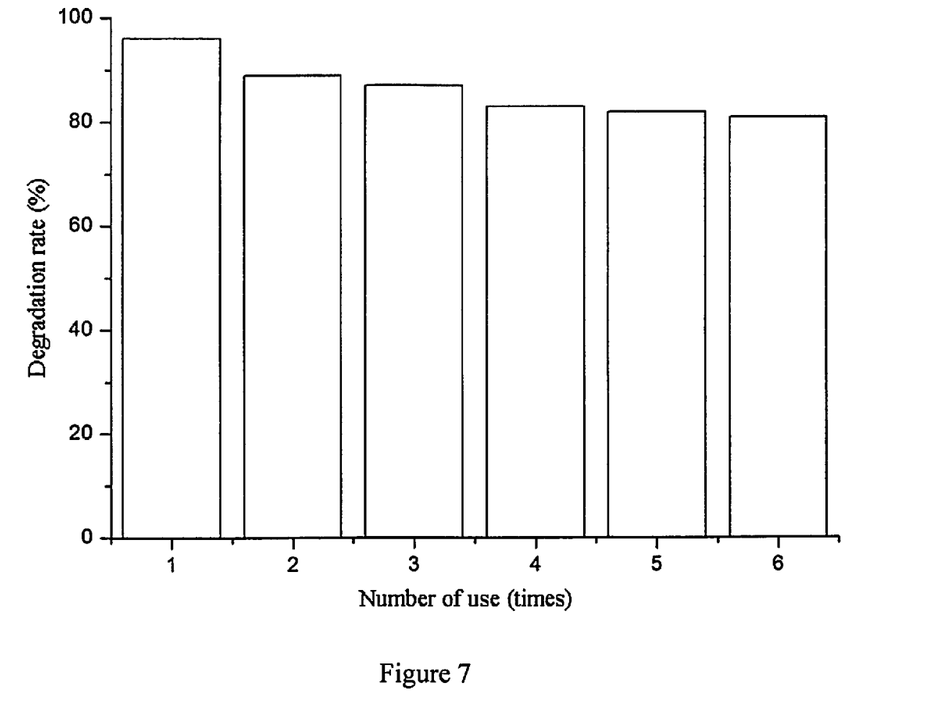
FIG. 7 shows the relationship between the reuse times and the degradation rate of kaolin in example 5.

After the kaolin were reused 5 times according to the above processes, it was found that the kaolin clays had a slightly reduction in the enhancing effects, and still had a significant promotion effect on the degradation rates, with the degradation efficiencies shown in FIG. 7.

As shown in FIG. 7, with the increase in the number of use, the increase effects of the adsorption and immobilization of the kaolin on the bacterial degradation capability were reducing. After reused 4~5 times, the degradation effects were reduced to approach 85% of the degradation efficiency of the free GY2B bacteria, but still had a significant increase in the degradation rate, therefore the used kaolin can be reused under certain conditions.

The above examples are the preferred embodiments of the present invention, but the embodiments of the present invention are not limited thereto, any other changes, modifications, alternatives, combinations, simplifications, made without departing from the spirit and the principles of the invention, all of which should be the equivalent replacement modes, will be included within the scope of the present invention.

The invention claimed is:

1. A method for preparing a composition comprising kaolin-immobilized *Sphingomonas* GY2B (GY2B) bacteria, comprising the steps of:
   (a) activating and growing a GY2B bacterial culture by culturing the GY2B bacteria in a phenol-containing enrichment medium to obtain a concentrated bacterial suspension;
   (b) centrifuging the concentrated bacterial culture;
   (c) washing the concentrated bacterial culture with a sterile physiological saline solution;
   (d) suspending the washed concentrated bacterial culture in a sterile physiological saline solution to obtain a bacterial suspension;
   (e) adding to the bacterial suspension a sterilized kaolin suspension comprising kaolin dissolved in a sterile MSM culture solution in an inoculation amount of 2-8%; and
   (f) incubating the preparation made in step (e) for 1-4 hours to adsorb and immobilize the GY2B bacteria on the kaolin, thereby preparing kaolin-immobilized GY2B bacteria.

2. The method according to claim 1, wherein the activation and growth of the GY2B bacteria in claim 1, step (a), is carried out as follows:
   (a) picking 1-2 GY2B colonies stored on a plate and inoculating it/them into a sterile MSM culture solution containing 50-200 mg/L phenol,
   (b) shaking the culture medium at 25-35° C. 100-200 rpm, in the dark, for 8-16 hours,
   (c) then removing 1-2 mL of the bacterial culture and subculturing in a fresh sterile MSM culture solution containing 50-200 mg/L phenol, for 8-16 hours, and
   (d) repeating the subculturing step of step (c) up to six times, to obtain GY2B bacteria having a stable ability to degrade phenol, and
   (e) plating and storing the GY2B bacteria made in step (d).

3. The method according to claim 1, wherein, in step (a), the phenol concentration in the medium is 50-200 mg/L, and wherein the GY2B bacteria are cultured for 8-16 hours.

4. The method according to claim 1, wherein the bacterial suspension obtained in step (a) is adjusted to have an absorbance at 600 nm ($OD_{600}$) of 0.8-1.5.

5. The method according to claim 1, wherein the centrifugation and washing steps are carried out at a temperature of 2-10° C., the centrifugation speed ranges from 6000-12,000 rpm, the centrifugation time ranges from 10-20 min. and the number of times for the centrifugation and washing steps ranges from 2-5.

6. A method according to claim 1, wherein the sterilization of the kaolin comprises:
   (a) autoclaving the kaolin at a temperature ranging from 100-150° C., for a time ranging from 15-60 min.,
   (b) drying the kaolin at a temperature of 80-150° C. for 10-30 min., and
   (c) dispersing the kaolin.

7. The method according to claim 1, wherein the kaolin has a mesh size of 100-300, and wherein step (f) is carried out in a constant-temperature shaking incubator at a speed of 100-200 rpm, at a temperature of 25-35° C., in the dark.

* * * * *